US006983183B2

(12) United States Patent
Thiagarajan et al.

(10) Patent No.: US 6,983,183 B2
(45) Date of Patent: Jan. 3, 2006

(54) METHOD AND APPARATUS FOR MONITORING CARDIAC PATIENTS FOR T-WAVE ALTERNANS

(75) Inventors: Srikanth Thiagarajan, Tustin, CA (US); Dongping Lin, Irvine, CA (US)

(73) Assignee: Cardiac Science, Inc., Irvine, CA (US)

( * ) Notice: Subject to any disclaimer, the term of this patent is extended or adjusted under 35 U.S.C. 154(b) by 454 days.

(21) Appl. No.: 09/904,914

(22) Filed: Jul. 13, 2001

(65) Prior Publication Data

US 2003/0060724 A1    Mar. 27, 2003

(51) Int. Cl.
*A61B 5/04*    (2006.01)
(52) U.S. Cl. .................................. 600/509; 600/515
(58) Field of Classification Search ............... 600/515, 600/513, 509
See application file for complete search history.

(56) References Cited

U.S. PATENT DOCUMENTS

| 5,148,812 A | 9/1992 | Verrier et al. |
| 5,265,617 A | 11/1993 | Verrier et al. |
| 5,437,285 A | 8/1995 | Verrier et al. |
| 5,560,370 A | 10/1996 | Verrier et al. |
| 5,570,696 A | 11/1996 | Arnold et al. |
| 5,713,367 A | 2/1998 | Arnold et al. |
| 6,735,466 B1 * | 5/2004 | Haghighi-Mood ........... 600/515 |
| 6,823,213 B1 * | 11/2004 | Norris et al. ................... 607/9 |

* cited by examiner

Primary Examiner—Mark Bockelman
(74) Attorney, Agent, or Firm—Gottlieb, Rackman & Reisman, P.C.

(57) ABSTRACT

A system to detect the presence or absence of T wave alternans is described based on statistical tests and periodicity transform. T wave and ST segment boundaries are detected in multi-lead ECG signals acquired from the regular clinical leads. Once the fiducial point and the above boundaries are delineated, computation of regular parameters like T wave amplitude, area under the T waves or segments of T wave, ST segment slope and/or the curvature of T wave are performed. Each parameter forms a rolling array of values with each successive beat. The array of values, or the time series, is used to make the decision about the T wave alternans. Two different methods are employed based on periodicity transforms and statistical tests. A set of numerical values (e.g. norm of the projection on to p-2 space, sums of adjacent terms after the trend removal, t-value, and number of deviations from alternans pattern) are all computed and compared to threshold values. Threshold values are computed from past information and experience with clinical databases and simulations. Final system comprises a software module, which can be part of the existing ECG monitoring programs as well as external defibrillator modules, apart from being stand-alone algorithms.

10 Claims, 9 Drawing Sheets

TWA ALTERNANS DETECTION BY A COMBINATION OF
STATISTICAL TESTS AND PERIODICITY TRANSFORMATION

FIG. 7

FIG. 8
ALGORITHM OF PERIODIC TRANSFORM METHODOLOGY

ALGORITHM OF STATISTICAL TESTS FOR ALTERNANS DETECTION

METHOD AND APPARATUS FOR MONITORING CARDIAC PATIENTS FOR T-WAVE ALTERNANS

BACKGROUND OF THE INVENTION

A. Field of Invention

This invention pertains to a method and apparatus adapted to monitor the intrinsic activity of a person to determine if the patient may be a candidate for cardiac disease. More specifically, the present invention pertains to a monitoring apparatus and method that analyzes the intrinsic cardiac signals from a patient to detect T-wave alternans, and use the same to derive an indication of the patient's cardiac condition.

B. Description of the Prior Art

One of the major objectives in cardiology is the identification of individuals who are prone to sudden cardiac electrical disturbances and whose hearts are electrically unstable. Proper and earlier identification of these individuals leads to a designation of these patients as potential candidates for either implantable or external cardioversion/defibrillation devices. Mass screening of individuals is instrumental in detecting the individuals with potential cardiac problems. Standard electrophysiological studies, though effective, usually involve invasive procedures [See Rosenbaum et al., 1996].

In the last few years, it has been found that T-wave alternans analysis is an effective method to predict the cardiac vulnerability to ventricular arrhythmia and sudden cardiac death. Three different approaches have been suggested for this analysis and several clinical and animal studies have validated its benefits. In a first approach, a group at MIT used a spectral method for estimation of T-wave alternans (TWA). Spectral analysis seems to indicate a definite peak at alternans frequency, despite the absence of visible ST/T-wave alternans on the surface ECG. In the original method by Smith et al., 1988, multiple spectra are generated during the analysis, each corresponding to a different part of the T wave. The signal registered at 0.5 cycles/beat indicates the ECG alternans and its magnitude quantifies the degree of alternans. Apparently a minimum heart rate of 100 beats/minute is needed for reliable detection of TWA using this technique. The respiration frequency peak is relatively variable and varies between 0.15 cycles/beat to 0.35 cycles/beat and is bound to create noise. Alternans measurement is done with reference to white noise/random noise, which is distributed through out the spectrum. The alternans voltage $V_{Alt}$ is calculated as follows:

$$V_{Alt} = (S_{0.5} - S_{Noise})^{1/2}$$

$V_{Alt}$ is measured in microvolts and $S_{0.5}$ and $S_{Noise}$ are the magnitudes of power spectrum at 0.5 cycles/beat and reference noise band respectively and are measured in microvolts squared. This value is normalized and compared with noise voltage to produce a unique measure (See U.S. Pat. No. 5,713,367, incorporated herein by reference).

However, there are several problems associated with this method. For example, the method is unable to localize the phase changes. An inherent problem in Fourier transform based methods is their inability to distinguish the noise or harmonics of the noise occurring at 0.5 cycles/beat. Several adjustments and pre-processing methods have been attempted to overcome these problems, including a known system of averaging signals between the different electrodes to remove the common motion artifact noise.

Problems related to the ectopic beats result in the phase reversals frequently which produces a decrease in spectral measurements due to the change in alternans pattern from an ABAB . . . type to a BABA . . . type pattern, where A and B may represent higher and lower values of T wave peak amplitude in a beat or any other similar parameters.

In another method suggested by Verrier R L and B D Nearing in 1992, a complex demodulation algorithm is used which assumes that the T-wave is a sinusoid of slowly varying amplitude at a frequency equal to alternans frequency and phase. The period from 60 to 290 ms following the apex of each R-wave was determined to coincide with the location of the T-wave. This period was divided into bins 10 ms wide for each successive beat, and the area between the ECG and the iso-electric baseline was computed for each 10 ms interval. A sixteenth order Butterworth filter was used for both de-trending and demodulating to remove the large low-frequency variation in T-wave area that occurs during occlusion and to leave a cleaner signal for spectral analysis. Several of the drawbacks in spectral analysis of the TWA are removed in this method and the complex demodulation takes into account the non-stationarity present in a time series.

Clinical studies indicate that the first half of a typical T-wave is much more sensitive to T-wave alternans then the second half (U.S. Pat. Nos. 5,842,997; 5,921,940). This factor combined with the fact that it is easier to detect T wave peaks than T wave boundaries make parameters like T wave peak amplitude and the area around the peak well suited for TWA analysis. Moreover, the estimation of such factors is less prone to delineation errors associated with T wave boundary errors.

Both these methods start with the assumption of sinusoidal varying alternans components and hence are different from the actual periodicity. The assumption of sinusoidal variations leads to the problems of harmonics of motion and respiration components interfering with this higher frequency component at 0.5 cycles/beat. In addition this technique utilizes elaborate filtering schemes and the entire processing results in a time domain equivalent of the spectral approach.

The third method of alternans estimation developed by Burattini et al., in 1995 is based upon the correlation analysis of individual beats relative to a median beat. This is also a time domain equivalent of spectral estimation and considered to be less in under-estimation compared to spectral methods. Time localization is possible in auto-correlation based methods, compared to the inability of frequency domain methods. However, the pre-processing needed for this method is as demanding as the other approaches discussed above.

Extensive clinical studies lead to the following conclusions regarding TWA.

(1) T-wave alternans are better predictors of ventricular arrhythmias than the potential ECG analysis and HRV analysis methods presently used.

(2) Patients with a positive microvolt T-wave alternans test were 13.9 times more likely to have a serious ventricular arrhythmia or to die than patients with a negative microvolt T wave alternans test.

(3) TWA analysis results are comparable to the electrophysiology studies relying on invasive procedures.

(4) The precise cellular and ionic basis for TWA is not precisely understood. Preliminary results indicate that beat-to-beat variations in action potential duration and action recovery interval are the cause of the TWA in surface electrocardiograms (Verrier and Nearing, 1994).

(5) T-wave alternans relate to a subtle change in the T-wave morphology that occurs in each alternate beat. TWA appear to reflect the occurrence of localized action-potential alternans, which creates dispersion of recovery, which in turn promotes the development of re-entrant arrhythmias.

In the last few years, several non-invasive methodologies have been suggested for predicting ventricular malignant arrhythmias. These methods include high frequency signal-averaged electrocardiography (SAECG) for late-potential analysis, heart rate variability and QT dispersion analysis (Gomes J et a., 1991; Day C P et al., 1990; Task Force of the ESC and the NASPE, 1996). These methods are limited in sensitivity and specificity in screening high-risk patients for ventricular arrhythmias and sudden cardiac death (SCD). Compared to these methods, T wave alternans have proved to be more reliable estimators and perform as well as invasive, electrophysiological studies in risk stratifying patients for life-threatening arrhythmias [Gold M et al., 2000].

Normal hearts exhibit alternans during very high heart rate, but diseased ones exhibit alternans, even during normal sinus heart rates. T wave alternans form part of repolarization alternans, while QRS alternans form part of depolarization alternans. QRS alternans show more correlation with heart rate and not with cardiac vulnerability. On the other hand, repolarization alternans, especially TWA, which primarily involves ST and/or T wave, have exhibited a consistent relationship with ventricular arrhythmias. Compared to other predictors of ventricular arrhythmias, TWA appears to be the only non-invasive technique having an efficacy comparable to that of electrophysiology labs. According to Rosenbaum DS et al., 1996, the challenge is to derive appropriate methodologies to detect "microscopic" T wave alternans in patients.

The fundamental premise in all three previous approaches is that TWA are related to the measurement of repetitions in the frequency or equivalent correlation domains. However, computational cost of these methods makes them difficult for real-time update with new beats. The time localization abilities of spectral domain methods is inferior compared to dynamic, time domain estimations. There is also a possibility that due to ectopic beats, a pattern reversal (from ABABAB . . . to BABABA . . . ) may occur. However, there is no efficient way to distinguish such a reversal in the frequency domain. The change in amplitude of the spectrum is related to both the duration and the amplitude of the alternans in an episode. In other words, the amount of alternation detected using the frequency domain methods is subject to the baseline/static portion of the time series (See U.S. Pat. Nos. 5,713,367; 5570696, incorporated herein by reference).

OBJECTIVE AND SUMMARY OF THE INVENTION

An objective of the present invention is to provide a method and apparatus that can be used for a quick and accurate indication of the cardiac condition of a patient.

A further objective is to provide an effective and accurate non-invasive method for detecting potential cardiac patients.

A further objective is to provide a diagnostic method and apparatus that can be readily implemented in patient monitors and cardiac devices without a need for the extensive redesign of the same.

Other objectives and advantages of the invention shall become apparent from the following description.

Briefly, the present invention is based on statistical methods and periodicity transforms to estimate the presence or absence of alternans. The presence or absence of alternans is derived from a statistical detection of periodicity and hence is better measured by statistical methods. The algorithm makes use of real-time calculation and can be easily updated every beat. This mode of calculation takes into account the non-stationarity present in the TWA and adapts to the situation. Multiple measures provide means to crosscheck the errors in the estimation and enable easy implementation with existing monitors or cardioverter-defibrillators equipment, apart from being standalone algorithms. Periodicity transforms provide direct measures to detect periodicity, which are unaffected by phase reversals caused by the ectopic beats.

The invention takes advantage of the basic assumption that the variations between the alternate beats, if significant and consistent, are indicative of the presence of alternans. The presence and characteristics of alternans are related to a difference between amplitudes of certain ECG parameters associated with alternate beats. Hence, the calculation of alternans is based on a reliable measure of periodicity. Periodicity transforms and statistical measures are better suited to detect the periodicity [Sethares and Staley, 1999]. The amount of pre-processing and manual interventions required to eliminate the effects of ectopic beats are Briefly, the present invention is based on statistical methods and periodicity transforms to estimate the presence or absence of alternans. The presence or absence of alternans is derived from a statistical detection of periodicity and hence is better measured by statistical methods. The algorithm makes use of real-time calculation and can be easily updated every beat. This mode of calculation takes into account the non-stationarity present in the TWA and adapts to the situation. Multiple measures provide means to crosscheck the errors in the estimation and enable easy implementation with existing monitors or cardioverter-defibrillators equipment, apart from being standalone algorithms. Periodicity transforms provide direct measures to detect periodicity, which are unaffected by phase reversals caused by the ectopic beats.

The invention takes advantage of the basic assumption that the variations between the alternate beats, if significant and consistent, are indicative of the presence of alternans. The presence and characteristics of alternans are related to a difference between amplitudes of certain ECG parameters associated with alternate beats. Hence, the calculation of alternans is based on a reliable measure of periodicity. Periodicity transforms and statistical measures are better suited to detect the periodicity [Sethares and Staley, 1999]. The amount of pre-processing and manual interventions required to eliminate the effects of ectopic beats are minimal in such methods. Periodicity transforms provide one of the best methods to detect hidden periodicity and are superior to Fourier transforms and complex demodulation based techniques. That is because the periodicity of alternans is not necessarily sinusoidal in nature. Fourier transform based methods start with the assumption that alternans are sinusoidal and hence need to deal with multiple noise sources. On the other hand, complex demodulation based methods suffer from large computational overload and neglects the periodicity aspect of the computation.

DETAILED DESCRIPTION OF THE INVENTION

T-wave alternans or TWA in a patient constitute a periodic phenomenon. In the present invention, several methods are derived in the time domain to estimate this periodicity and to derive indices that may be used to determine, for example, if TWA are present, and consequently, whether the patient is prone to, or even suffering from tachyarrhythmia. More particularly, the invention makes use of the traditional statistical theory to derive several tests indicative of alternans. The results from one or more of these tests are used to make a determination about the patient and his cardiac condition.

Figure 1:
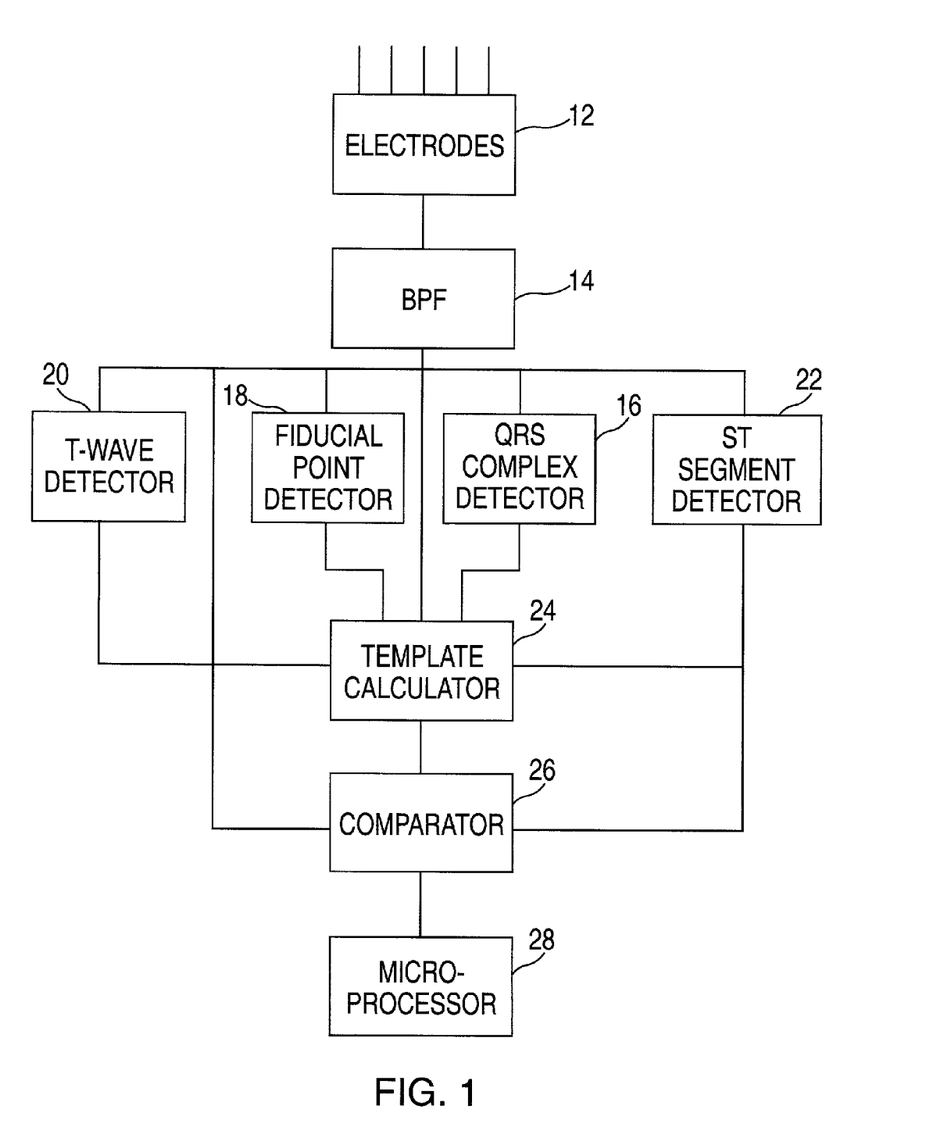
FIG. 1 shows a block diagram of an apparatus used to detect the presence of TWA in accordance with this invention.
Figure 2:
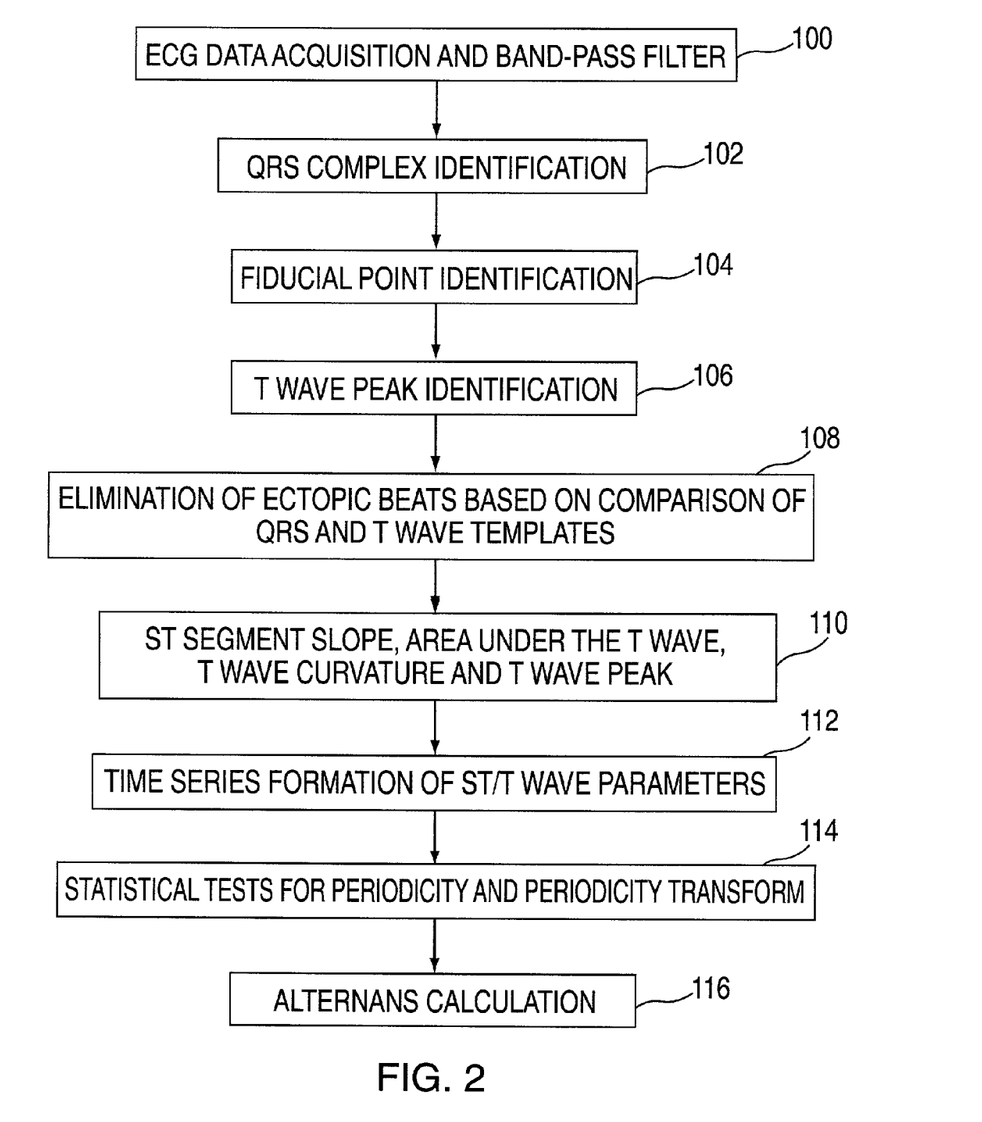
FIG. 2 shows a flow chart for the subject method.
Figure 2A:
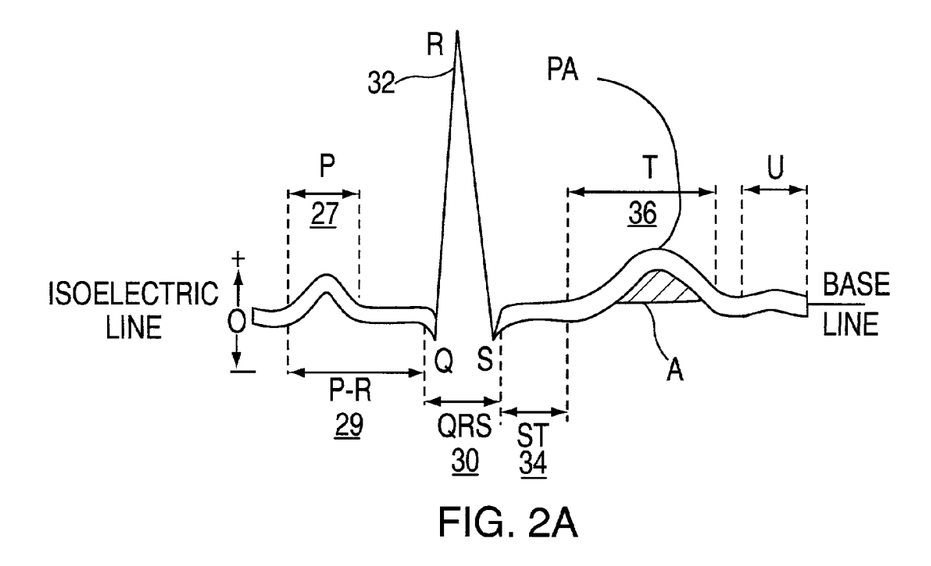
FIG. 2A shows the ECG for a single heart beat illustrating its various components.
Figure 2B:
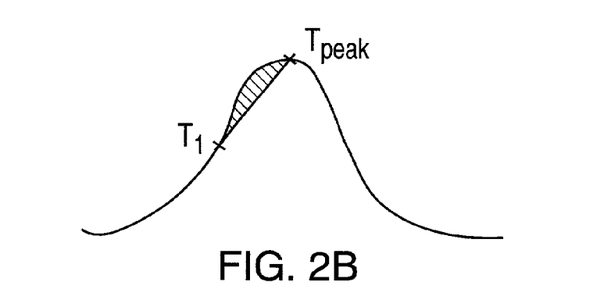
FIG. 2B shows a portion of a T-wave and how a curvature thereof is determined in accordance with this invention.
Figure 2C:
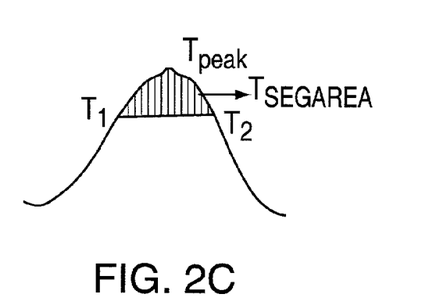
FIG. 2C shows a portion of a T-wave and how a partial area under the curve is determined in accordance with this invention.

A preferred method and apparatus for performing tests based on statistical analyses of ECG parameters are illustrated respectively in FIGS. 1 and 2. FIG. 1 shows a block diagram of a cardiac monitoring apparatus 10. The apparatus 10 includes a set of standard electrodes 12 that are attached to a patient in the standard chest lead positions for sensing ECGs. The signals from the electrodes are conditioned by a band pass filter (BPF) 14 and the resulting ECGs are fed to several detector algorithms, including a QRS complex detector 16, a fiduciary point detector 18, a T-wave detector 20, an ST segment detector 22 and a template calculator 24. The device 10 further includes a comparator 26. These elements are coupled to a microprocessor 28 that is programmed to analyze the ECG signals and the signals generated by the elements 16–26 to generate parameters indicative of TWAs. It should be understood the elements 16–26 are shown as discrete elements which, in actuality, may be implemented by software for the microprocessor 28.

FIG. 1A shows a typical ECG signal that is sensed by the electrodes 12. The signal includes a QRS complex 30, including an R-wave 32, an ST segment 34 and a T-wave 36.

The operation of the apparatus 10 shown in FIG. 1 is now described in conjunction with the flow chart of FIG. 2. In step 100 the apparatus 10 of FIG. 1 captures an ECG signal, such as the one shown in FIG. 1A. The ECG is conditioned by BPF 12.

In step 102 the QRS detector 16 identifies the QRS complex 30, including R-wave 32. Algorithms for this purpose are well known in the art and will not be described here.

In step 104 the fiducial point detector 18 identify a predetermined fiducial point related to the QRS complex 30. Preferably the fiducial point identified is the peak of the R-wave 32 and therefore in step 104 the position and magnitude of the R-wave is determined and used for defining the fiducial point.

In step 106 the immediate wave following the QRS complex 30 is identified as the T wave 36. More specifically, the T wave 36 is identified by a smooth continuous and steady rise in amplitude with respect to the baseline. The T wave detector 20 may also identify the T wave peak point PA. For this purpose, the detector 20 includes a two-stage process (not shown). The first stage of the processor is a low-pass smoothening filter that eliminates minor high frequency noise by averaging. The second stage of the T wave detector process is a peak detector. The peak detector first identifies a local peak for sequential segments of the identified T wave 36. A local peak is identified as a point surrounded by three decreasing amplitude points on either side of the peak point and all of them above a particular threshold compared to local baseline and associated with a sign change in the derivative at that point. The threshold value is based on T peak values of previous beats and the fiducial point amplitude 32. At the end of the T-wave, the amplitudes of the local peaks are compared and the local peak with the highest amplitude is used as the peak point PA.

As the monitoring apparatus processes successive ECG beats, characteristics of the corresponding T-waves, including for instance their end point locations, localized peaks and peak points are recorded. A T-wave template is then generated from this data by template calculator 24, for example, by averaging the data from the last six or eight beats. More specifically, the ST segment and T wave are overlapped with templates derived from previous six to eight beats to minimize the errors in T wave peak and T wave end point locations. T wave templates are periodically generated to accommodate the changing morphology. Templates also help to eliminate those beats with abnormal ST/T wave parameter values. A set of possible templates are shown in FIGS. 3A–3H with asterisks (*) indicating the respective T-wave fiduciary points. These T wave fiducial points are manually selected, using for example a graphical user-interface available from Matlab® software. The endpoints of the T waves are the end-points of the templates. Algorithm used in the present invention exactly matches with the manual T wave locations by the experts.

In step 108 the ST segment of the current ECG (detected by ST segment detector 22) and the current T-wave are compared to the average ST segment and the T-wave of the template. If the current ECG includes an ST segment and T-wave which is markedly different from the template previously determined or the average ST segment, then no further analysis is performed on the ECG, towards the detection of T wave alternans. In effect, the particular beat is neglected. Heart rate variability (or) variations between successive RR intervals usually has minimal impact on the ST segment and T wave duration and therefore the comparison between the current ST segment and T-wave and the previous corresponding measurements and template eliminate the errors.

Figure 3A:
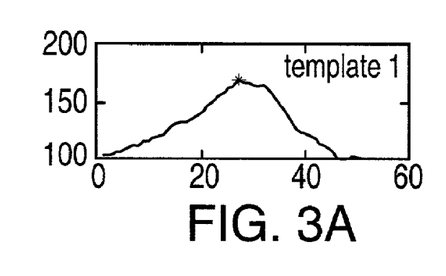
FIGS. 3A–H show a plurality of templates for T-waves.
Figure 3B:
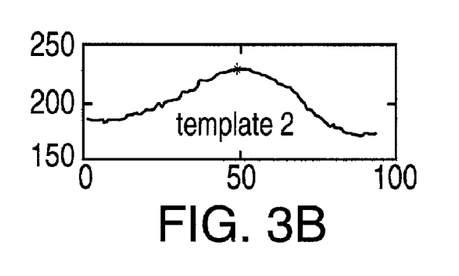

Next, in step 110 a set of parameters indicative of TWA are generated by the microprocessor 28. These parameters may include (i) The area A under the T wave ($T_{area}$), as indicated in FIG. 3B. This area A is calculated as follows $$T_{area} = \sum_{i=Tstart}^{Tend} T(i)$$

where $T_{start}$ is the starting point of the T wave and the $T_{end}$ is the end point of the T wave.

(ii) Amplitude of the T wave peak ($T_{peak}$): The peak amplitude of the T wave is $$T_{peak} = \max\{T(i)\}_{Tstart}^{Tend}$$

(iii) Curvature area of T wave ($T_{curve}$): This parameter indicates the area at a curvature as shown in the FIG. 3B. Once the T wave peak is detected, a point T1 a fixed duration before the T wave peak is chosen. A straight-line approximation is used to fit the two points and the amplitudes of the points in between are estimated. The difference between the sums of the amplitudes of the linear interpolated points and the amplitudes of actual points provide the curvature area of T wave.

(iv) ST segment slope: This parameter, $ST_{slope}$, is measured as the mean slope between the end of S wave and T wave starting point, as can be seen in the ECG beat.

Figure 3C:
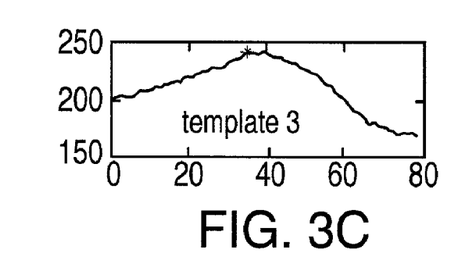
Figure 3D:
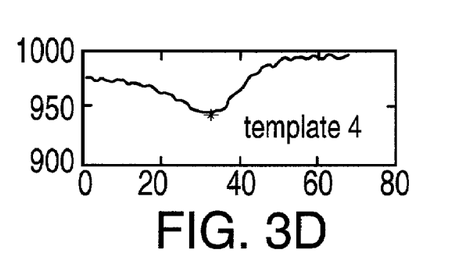
Figure 3E:
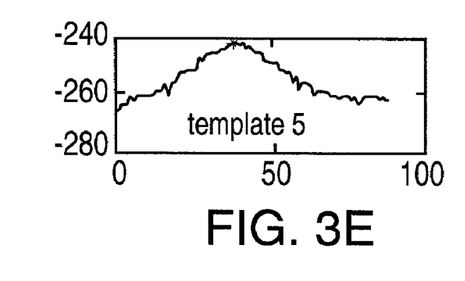
Figure 3F:
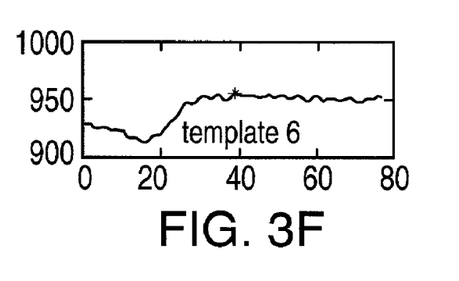
Figure 3G:
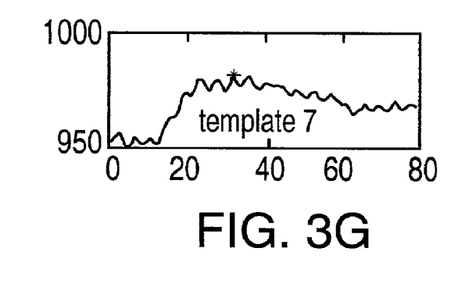
Figure 3H:
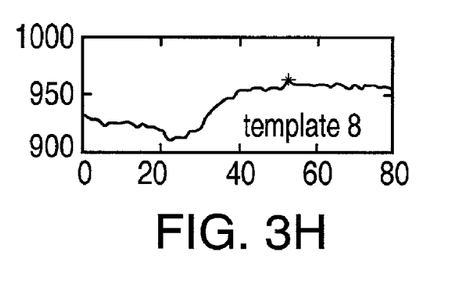

(v) Areas of smaller segments inside ST/T wave period ($T_{segarea}$) This $$T_{segarea} = \sum_{i=T_1}^{T_2} T(i)$$

parameter calculation is similar to parameter (i). For example, area of the T wave around the peak can be defined as where $T_1$ and $T_2$ are points equidistant away from peak (See FIG. 3C).

The values of above parameters from all the beats are accumulated in step 112 to define respective time series For example, once the first 32 beats are available, a time series of the form shown below is used for further analysis.

$T_{peak} = \{T_{peak}(1), T_{peak}(2), T_{peak}(3), \ldots, T_{peak}(32)\}$;
$T_{area} = \{T_{area}(1), T_{area}(2), T_{area}(3), \ldots, T_{area}(32)\}$;
$T_{curve} = \{T_{curve}(1), T_{curve}(2), T_{curve}(3), \ldots, T_{curve}(32)\}$;
$T_{segarea} = \{T_{segarea}(1), T_{segarea}(2), T_{segarea}(3), \ldots, T_{segarea}(32)\}$;
$ST_{slope} = \{ST_{slope}(1), ST_{slope}(2), ST_{slope}(3), \ldots, ST_{slope}(32)\}$.

Several different tests are next performed (step 114) and the results of these tests are used to arrive at a decision regarding the presence or absence of alternans. The amplitude of alternans is calculated, if present (step 116). Ectopic beats are eliminated by a measure based on the overlap (i.e., comparison with the template) and subtraction criterion as indicated below.

$$C_m = \sum_{i=q1}^{i=q2} (qrs(i) - \text{template}(i))$$

The value $C_m$, can be estimated as an indirect measure of correlation between a template of a normal QRS complex and an incoming QRS complex. The incoming QRS complex is aligned with the template with respect to R point and a subtraction carried out for a fixed number of samples on either side, between the indices $q_1$ and $q_2$. Less than 30 seconds of ECG beats are required to arrive at a reliable measure due to the multiple statistical measures. With each new incoming beat, the T wave parameter series can be updated. An update is possible with the availability of every new fiducial point location.

In one embodiment, four different statistical tests and a test using periodicity transform are utilized to arrive at the final decision regarding the presence or absence of alternans. These tests are described in more detail below. The final amplitude of the TWA is then determined based on the difference between waveform peak, shape and area between the adjacent beats, as defined in original visual methods [Lewis T., 1910; Kalter and Schwartz, 1948]. The mean, maximum and minimum values of the alternans provide descriptions or characteristics of the alternans, if they are considered present.

Test 1: Test for Difference in Means

This test makes use of the simplest definition of TWA. Alternate beats in ECG recordings show differences in the T wave, including the ST segment. Hence, a basic parameter is the measure of the difference between the means in the two groups of data, as defined by the time series. Two groups of data are formed by odd and even beats. For example, group I can be made of the parameter T peak values of the odd beats and group II can be made of the parameter T peak values in even beats. Then the two series can be represented as $X_I = \{T_{peak}(1), T_{peak}(3), T_{peak}(5), \ldots\}$ and
$X_{II} = \{T_{peak}(2), T_{peak}(4), T_{peak}(6), \ldots\}$ The standard t test is the easiest and the most conventional statistic for measuring the significance of the difference of means. Several useful references on statistics provide exhaustive information about the t-test. The actual value of the t-statistic is calculated as follows:

$$t = \frac{\bar{x}_I - \bar{x}_{II}}{S_D/\sqrt{N}}$$

where the standard deviation, $S_D$, is calculated as follows:

$$S_D^2 = \frac{\sum_{n \in I}(x_n - \bar{x}_I)^2 + \sum_{n \in II}(x_n - \bar{x}_{II})^2}{N_I + N_{II} - 2}\left(\frac{1}{N_I} + \frac{1}{N_{II}}\right)$$

where, $N_I$ = the number of elements in group I and
$N_{II}$ = the number of elements in group II.

All other parameters discussed above can also be grouped into similar two groups as $X_I$ and $X_{II}$. Then, the evaluation of the significance of this t value with $N_I + N_{II} - 2$ degrees of freedom is done with look-up table of t values. For example, for $N_I = 64$ and $N_{II} = 64$, we get $t_{126,0.1} = 1.658$; $t_{126,0.05} = 1.980$; $t_{126,0.02} = 2.358$; $t_{126,0.01} = 2.617$;

The values differ for different values of degrees of freedom. Based on a comparison of t-value with the above values from table, a discrete score is calculated.

For computing any statistic, it is necessary to use observations obtained from a sample (or) time series as well as certain population parameters. If these parameters are unknown, they must be estimated from the time series. The number of degrees of freedom of a statistic generally defined as the sample size (or) number of elements in time series N, minus the number of population parameters (k) which must be estimated from sample observations. In symbols, v=N−k, where v indicates the degrees of freedom. For estimating the t value with two groups I and II, with number of elements $N_I$ and $N_{II}$ respectively, and k=1 for each mean estimation. Hence, the total degrees of freedom becomes $v=(N_I-1)+(N_{II}-1)$.

The fraction indicates the significance value, and is the probability that [t] could be this large or larger by chance, for distribution with equal means. Therefore, a small numerical value of the significance, like 0.01, means that the observed difference is "very significant". This is a direct measure of the TWA, compared to the frequency domain measures.

Localized trend removal precedes the calculation of T values. Localized trend removal is possible with multi-point averaging and removal of the local means. A process is shown in equation below illustrates the trend removal process.

$$y(n) = x(n) - (1/N) \sum_{i=n-N}^{n} x(n)$$

The number of points N are chosen based on the trend and also as an even number in order to account for alternating values.

Test 2: Test for Sum of Adjacent Values

Any time series $X_t$ can be regarded as a combination of a trend component $m_t$, a seasonal component $s_t$, and a stationary random noise component $N_t$ [Brockwell and Davis, 1987]. This is true for the time series formed by the values of T wave peaks and other parameters in ECG beats. Here again, the input series $X_t$ are formed by $\{T_{peak}(1), T_{peak}(2), T_{peak}(3), T_{peak}(4), \ldots\}$ or one of the other T wave parameters. There may be slower seasonal components also in the time series formed by ST/T wave parameters in continuous beats. Trend component is a slowly changing function $m_t$ and the seasonal component $s_t$ is a function with a known period d.

$$X_t = m_t + s_t + N_t$$

Another assumption is $s_t = s_{t+2}$ for the seasonality due to alternans; once the linear trend and the mean component is removed, sum of the adjacent values in TWA series should be nearer to zero for the presence of alternans. In other words, a series of sums of adjacent values should be closer to zero. This makes an assumption that all other components are removed.

A time series with 32 elements $X_t = \{x_0, x_1, x_2, x_3, \ldots\}$ is converted to $Y_t = \{x_0+x_1, x_1+x_2, x_2+x_3, \ldots\}$. Two different hypotheses are verified here.

Hypothesis 1: $mean(Y_t) = 2*mean(X_t)$ if the trends $m_t$ are not removed. The trend component here includes the removal of mean of the time series.

Hypothesis 2: $mean(Y_t) = 0$ if the trends $m_t$ are removed

Both the above hypotheses are verified by performing a t-test for the modified series $Y_t$. A scoring system based on the t-table values is introduced as in simple t-test above to calculate a discrete score.

Test 3: Rayleigh Test for Periodicity

The presence of a periodicity in a time series can be investigated using the Rayleigh Test. In the alternans, the periodicity of interest is of order 2. Every other beat has similar T wave parameter in the case of alternans. In the context of alternans, one can calculate a parameter, r, that indicates the regularity of the phase reversal present in alternans, a percentage amount. This calculation is performed over all the values of 0 to N, the length of the sequence. Rayleigh test, in essence, is used to test the hypothesis that the distribution around the unit circle is uniform versus the hypothesis that it follows a random distribution [Mardia, 1972].

In the context of alternans, this is simply a method to describe if the observed time series follows a periodic pattern or not. Initial step involves the generation of a statistic based on simulations. The comparison is done by generating a sequence of normally distributed random numbers of length equal to the length of measured time series (i.e) (number of beats in estimation=32) and computing the number of times the random sequence satisfies the alternans characteristics. This is repeated multiple times to arrive at the probability that this occurrence is possible by noise or a set of random numbers. An assumption is made that the T wave parameters satisfy normal distribution [Elghazzawi and Geheb, 1997].

A table of Raleigh measures based on observations of 100000 randomly generated sequences of length=32, provides the following probability values. In other words, these values indicate the chance of alternans happening in a random sequence of 32 beats. Alternans is defined here in terms of either [ABAB . . . ] or [BABA . . . ] patterns, a two-way probability measure. A scoring system is again used to indicate the presence of alternans, based on the number of times, the observed time series, deviates from the alternans pattern.

| Deviations | 0 | 1 | 2 | 3 | 4 | 5 | 6 | 7 | 8 | 9 | 10 | 11 | 12 |
|---|---|---|---|---|---|---|---|---|---|---|---|---|---|
| Chance | 0.000 | 0.0000 | 0.0000 | 0.0000 | 0.0000 | 0.00003 | 0.00040 | 0.00125 | 0.0045 | 0.01250 | 0.02940 | 0.06000 | 0.10250 |

For example, if a series of T wave peak values from 32 consecutive beats show a pattern such that $\{T_{peak}(1) > T_{peak}(2), T_{peak}(2) < T_{peak}(3), T_{peak}(3) > T_{peak}(4), T_{peak}(4) < T_{peak}(5), \ldots\}$ for 32 beats without a single deviation, then the score for the presence of alternans is (1−chance)*100=100%, based on the above table (i.e) Deviation=0. Otherwise, if the pattern deviates 7 times out of 32 beats, then the score for the presence of alternans reduces to (1−chance)*100=99.875% and so on. All other parameters from T wave like $T_{area}$, $T_{segarea}$, $ST_{slope}$ can also be used in the same way.

Test 4: Number of Zero Crossings of the Alternans

This is another measure to detect the occurrence of the alternans in real time. This provides a measure equivalent to the number of zero crossings in any time interval. T wave alternans, is modulated by the effects of parasympathetic and sympathetic stimulation and also by the respiration effects.

Hence, these effects cause slow variations across the alternans measure. Instead of performing the other calculations directly, slow moving trends can be removed by the subtraction of the mean of even (for example, 6 or 8 or 10) number of beats.

Since the aim is only to determine the presence or absence of a periodic component at 0.5 cycles/beat, the number of zero crossings provides an approximate indication of the periodicity. This measure is equivalent to Rayleigh's test for periodicity. Removal of localized trend as described in the Test 1 is the initial step. When the slow trends are removed, the series $X=\{x_1, x_2, x_3, x_4, \ldots\}$ follows a pattern of $\{x_1>0, x_2<0, x_3>0, x_4<0, \ldots\}$ or $\{x_1<0, x_2>0, x_3<0, x_4>0, \ldots\}$ and so on. The time series X can be made of any of the T wave parameters; for example, $\{T_{peak}(1), T_{peak}(2), T_{peak}(3), T_{peak}(4), \ldots\}$ and so on. Under ideal conditions, the presence of alternans will mean (N−1) zero crossings for a length of N beats. A scoring system can be introduced which indicates the number of actual zero crossings.

Test 5: Periodicity Transform

Calculations related to TWA involve periodicity. In other words, a series of T wave parameters should show the presence of a periodic component with period=2, for confirming the presence of alternans. The periodicity transform (PT) can be used to decompose sequences into a sum of small-periodic sequences by projecting onto the periodic subspaces $P_p$. The problem of identifying alternans in this context is related to identifying the periodicity and its significance. Like the process of auto-correlation, the periodicity transform is inherently a time domain operation, but is not equivalent to the power spectrum. Periodicity transform is linear in period, rather than linear-in-frequency or linear-in-scale. Periodicity transform finds its own set of basis elements.

Mathematical Background

A sequence of real numbers $x(k)$ is called p-periodic if $x(k+p)=x(k)$ for all integers k. Let $P_p$ be the set of all p-periodic sequences, and P be the set of all periodic sequences. Both $P_p$ and P are closed under addition, scalar multiplication and so on. In order to project sequences P onto $P_p$, consider the inner product from P×P into R defined by $$\langle x, y \rangle = \lim_{k \to \infty} \frac{1}{2k+1} \sum_{i=-k}^{k} x(i)y(i)$$

for arbitrary elements x and y in P. For the purpose of calculation, if x is of period $p_1$ and y is of period $p_2$, then the sequence $x(i)y(i)$ is $p_1 p_2$ periodic, and the above equation becomes the average over a single period, (i.e.)

$$\langle x, y \rangle = \frac{1}{p_1 p_2} \sum_{i=0}^{p_1 p_2 - 1} x(i)y(i)$$

The associated norm is $$\|x\| = \sqrt{\langle x, x \rangle}$$

Projection onto Periodic Subspace

The primary reason for stating this problem in an inner product space is to exploit the projection theorem. Let $x \in P$ be arbitrary. Then a minimizing vector in $P_p$ is an $x_p^* \in P_p$ such that $$\|x - x_p^*\| \leq \|x - x_p\|$$

for all $x_p \in P_p$. Thus $x_p^*$ is the periodic vector "closest to" the original x.

The Projection Theorem [Luenberger]

Let $x \in P$ be arbitrary. A necessary and sufficient condition that $x_p^*$ be a minimizing vector in $P_p$ is that the error $x - x_p^*$ be orthogonal to $P_p$.

Since $P_p$ is finite (p-dimensional) subspace, $x_p^*$ will in fact exist, and the projection theorem provides a way to calculate it. The optimal $x_p^* \in P_p$ can be expressed as a linear combination $$x_p^* = \alpha_0 \delta_p^0 + \alpha_1 \delta_p^1 + \ldots + \alpha_{p-1} \delta_p^{p-1}$$

where the sequences $\delta_p^s$ for $s=0,1,2,\ldots,p-1$ are the p-periodic orthogonal basis vectors $$\delta_p^s(j) = \begin{cases} 1 & \text{if } (j-s) \bmod p = 0 \\ 0 & \text{otherwise} \end{cases}$$

Most standard transforms can be interpreted as projections onto suitable subspaces, and in most cases (such as the Fourier and Wavelet transforms) the subspaces are orthogonal. Such orthogonality implies that the projection onto one subspace is independent of the projection onto others. Thus a projection onto one sinusoidal basis function (in the Fourier Transform) is independent of the projections onto others, and the Fourier decomposition can proceed by projecting onto one subspace, subtracting out the projection, and repeating. Orthogonality guarantees that the order of projection is irrelevant. This is not true for projection onto non-orthogonal subspaces such as the periodic subspaces $P_p$.

Thus the order in which the projections occur effects the decomposition, and the PT does not in general provide a unique representation. Once the succession of the projections is specified, however, then the answer is unique. In the present invention, the projection is first done onto P-1 space, and then to P-2 space and so on. Hence, the non-orthogonality is only a theoretical constraint; it is not a practical problem. The Periodicity Transform searches for the best periodic characterization of the time series $X_t$ of length N. $X_t$ can be a series of T wave peaks $\{T_{peak}(1), T_{peak}(2), T_{peak}(3), \ldots\}$ or other T wave parameters.

The underlying technique is to project $X_t$ onto some periodic subspace giving $X_p = \pi(X_t, P_p)$, the closest p-periodic vector to $X_t$. This periodicity is then removed from $X_t$ leaving the residual $r = X_t - X_p$, stripped of its p-periodicities. Both the projection $X_p$ and the residual $r_p$ may contain other periodicities, and so may be decomposed into other q-periodic components by further projection onto $P_q$.

In T wave alternans calculation, the purpose is to calculate a simple measure of periodicity. Ideally, the available algorithms calculate only the $2^{nd}$ alternation and using the periodicity transform based algorithms, it becomes easier to compute the $2^{nd}$ and $3^{rd}$ alternans easily. The following steps provide a way to pick the alternans;

(i) Assume a threshold T.
(ii) Calculate the projections $X_t = \pi(X, P_p)$
(iii) Let p=1.

(iv) Remove the linear trend by removing the projection onto p=1.
(v) Let p=2.
(vi) Check to see if the projection contains at least T percent of the energy in X.
(vii) If it has T percent of the energy, choose $X_p$ as the basis element.
(viii) If necessary, calculate the other periodicities.

Figure 4:
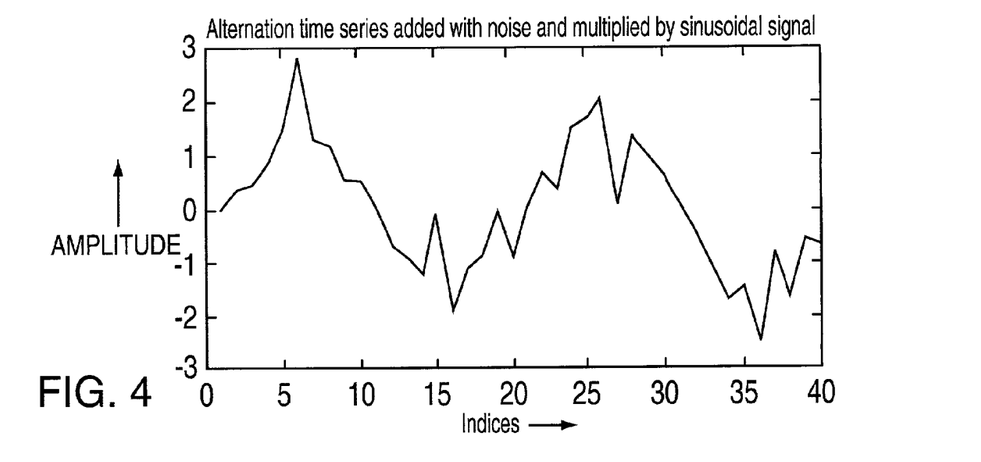
FIG. 4 shows an alternant time series with noise superimposed on a sinusoidal signal.

FIG. 4. shows a typical alternation time series added with noise and multiplied by a sinusoidal slowly varying signal; x axis represents the number of beats and the y axis represents the amplitude of T wave parameters.

There are variations possible in the algorithm to highlight the periodicity of two or three alone. We are neglecting the periodicity of p=1 as irrelevant. With the above signal subjected to periodicity transform, beginning with p=2, we get the results as follows: Power contained in the projection onto each periodicity is listed in the table below. For example 0.015*100=1.5% of the power of the above waveform is contained in periodic component with period 8. Periodic component at p=18 seems to contain the maximum fraction of the total power, around 6.19%.

| Period | 8 | 9 | 10 | 11 | 14 | 15 | 16 | 17 | 18 | 19 | 20 |
|---|---|---|---|---|---|---|---|---|---|---|---|
| Power | 0.015 | 0.039 | 0.018 | 0.0216 | 0.0169 | 0.0282 | 0.0342 | 0.0471 | 0.0587 | 0.0619 | 0.0597 |

When the waveform is smoothened with eight-point averaging, to eliminate the respiratory artifact, the results are as in table below. Here the power in periodic component at p=2 is maximum, showing the presence of alternans.

| Period | 2 | 6 | 7 | 9 | 10 | 11 | 12 | 13 | 14 | 15 | 16 | 17 | 18 | 19 | 20 |
|---|---|---|---|---|---|---|---|---|---|---|---|---|---|---|---|
| Power | 0.035 | 0.015 | 0.022 | 0.029 | 0.015 | 0.023 | 0.022 | 0.012 | 0.020 | 0.023 | 0.027 | 0.029 | 0.029 | 0.029 | 0.029 |

Usually the search goes on till p=N/2, but for the TWA analysis, the search can be stopped at p=3; the accurate value of the threshold can be arrived at based on the results with multiple iterations and the size of the data. Another variation can find all the projections onto higher-periodic spaces like p=4,6,8, . . . ,N/2, and try to extract the p=2 component and add them. Limiting the length of a segment allows to eliminate the slow variations and for consistent estimations, a rolling set of estimations are done. Limiting the length to 16 beats in the time series at a time provides a break from respiration induced slow oscillations.

Figure 5:
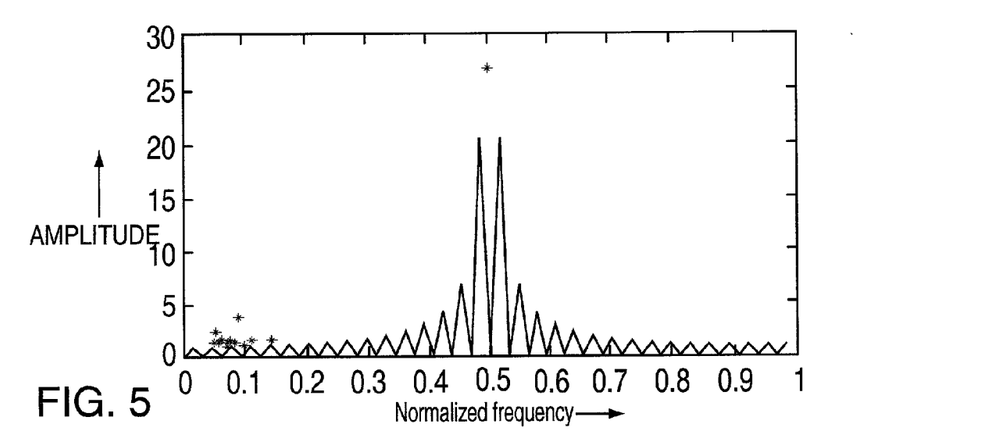
FIG. 5 shows the effect of phase reversal on the spectral amplitude calculation. The plot with * marks indicates the energy calculation based on periodicity transform.
Figure 6:
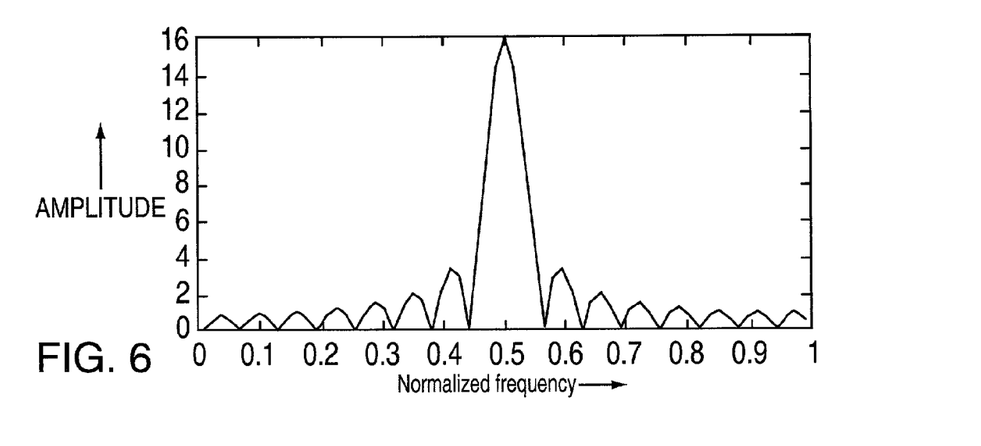
FIG. 6 shows the decrease in spectral amplitude when a phase change happens at three-quarters of the length of the time series.

Another advantage is illustrated here. When a pattern change happens, like [ABAB . . . ] changes to [BABA . . . ] in the middle of the sequence, the following change in spectrum results, as shown in the FIG. 5. The power gets reduced at $f_s=0.5$ cycles/beat and almost becomes zero. However, using the periodicity transform, the change in the sequence has no effect and the periodicity with p=2 contribute the maximum percent to the energy, as represented by * in the plot. When the change happens only at the final quarter, the spectrum is shown to have a reduced amplitude peak as shown in FIG. 6. Periodicity transforms are less affected by such phase changes.

This is a major problem in using a data segment or episode for the calculation of frequency spectrum. There is no clear distinction whether the spectral amplitude or the power is indicative the alternans magnitude or the duration or both. As far as the alternans is concerned, the measure should be indicative of the amount of the alternans. Periodicity transforms can be suitably modified to provide a unified normalized measure irrespective of the length of the signal.

Specific Advantages

If two signals x(t) and y(t) have their spectra non-overlapping, then the signals can be recovered easily using linear filters. For example, the signals can be the time series x(t) formed by T wave peaks like $\{T_{peak}(1),T_{peak}(2),T_{peak}(3), . . . \}$ and y(t) may be a noise time series due to respiration induced artifact. However, if their spectra overlap significantly, the linear methods fail. On the other hand, periodicity transform looks for specific periodicities and is able to separate them. Even with added random noise, periodicities, which are not known apriori, are separated. PT provides a way of finding simple harmonic templates that may be obscured by the inherent complexity of the spectrum, and the process of subtracting the projection from the original signal can be interpreted as a multi-notched filter that removes the relevant fundamental and its harmonics. It has also been proved that a deterministic, periodic process can be detected when surrounded by a random sequence and these properties open up a new way of eliminating several constant frequency noises as well as random noise sources, related to alternans and also ECG signals, in general [Sethares, 1999].

Implementation Details

Figure 7:
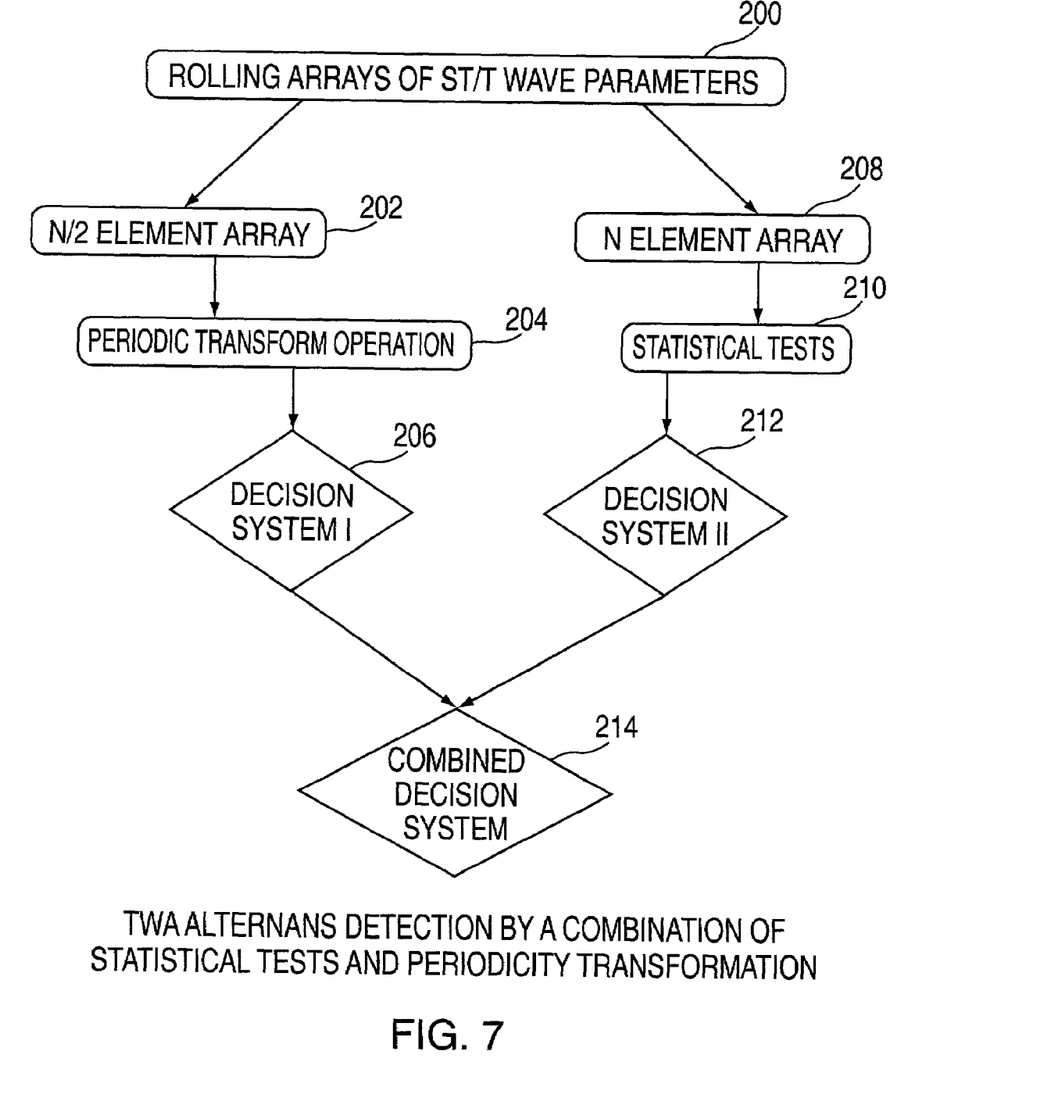
FIG. 7 shows a flow chart of how a decision is made using both statistical and periodic transform methodologies.

The final three steps 112, 114, 116 of the flow chart of FIG. 2. can be expanded as follows. Referring to FIG. 7, in step 200 the latest members of the relevant time dependent series are determined as discussed above. In step 202 the periodic transform test (test 5) is performed by generating the N/2 element array or series (step 204), performing the periodic transform (step 204), making a decision I as to whether TWA are present.

Figure 8:
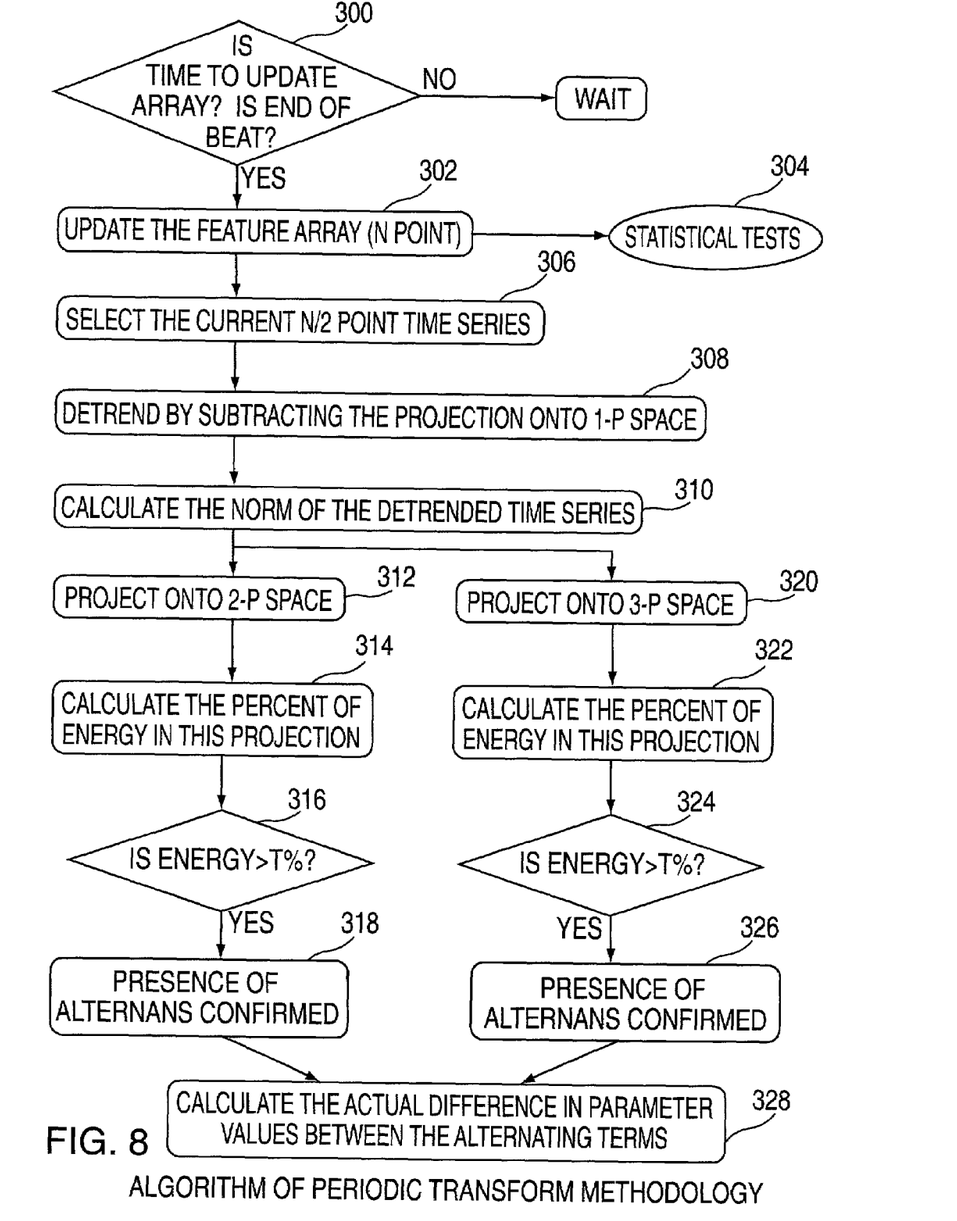
FIG. 8 shows details of a periodic transform methodology.
Figure 9:
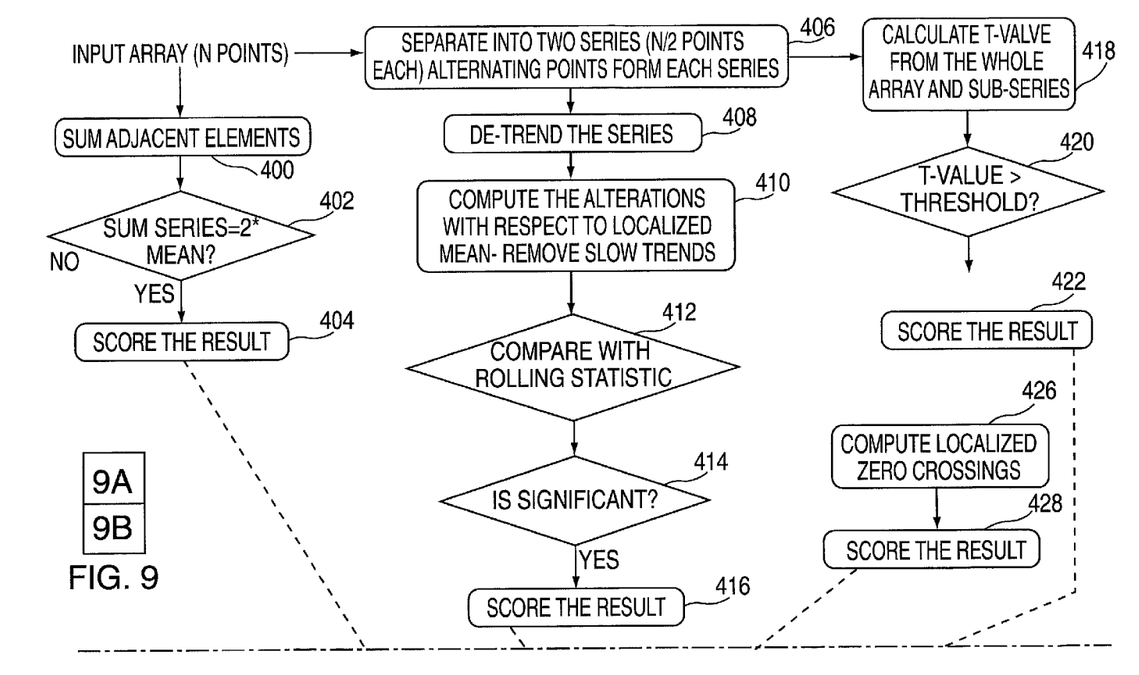
FIG. 9 shows details of several statistical test methodology.
Figure 9B:
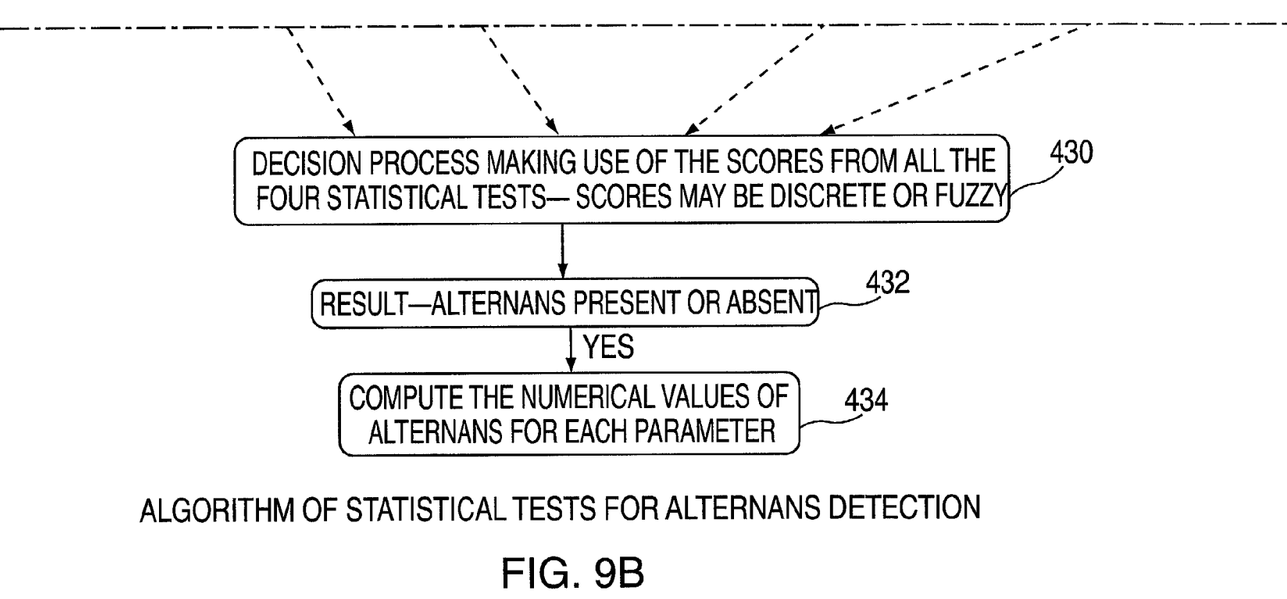

FIG. 8 shows a flow chart of the computations performed as part of the periodic transform while FIG. 9 shows a flow chart of the computations for the statistical tests. In FIG. 8, step 300 a determination is made on whether there is new data. In step 302 the data series is updated. In step 304 the series is provided to the statistical tests described below in conjunction with FIG. 9.

In step 306 the current series of N/2 members is selected. In step 308 a detrend operation is performed by subtracting the projections in 1-p space as discussed above. In step 310 the norm of the series is determined. Instep 312 the series is projected into 2-p space. In step 314 the percentage of energy in the subject projection is determined. In step 316 this energy is compared to a threshold level T %. if the energy level exceeds this level, then in step 318 the presence of TWA is confirmed.

As seen in FIG. 8, the series from step 310 is also projected into a p-3 space and steps 322, 324 and 326 (similar to steps 314, 316, 318) are performed to make an independent confirmation of TWA. In step 328 the differences in the values between alternating terms is determined.

In FIG. 9, the series is processed by summing adjacent components (step 400), testing to see if this sum is equal to double the mean (step 402). If it is then the result is scored in step 404.

The series is also separated into two separate series of N/2 members each in step 406, the series are detrended (step 408). In step 410 the alternations with respect to the localized mean is determined and slow trends are removed.

In step 412 the rolling statistics for successive beats are analyzed. In step 414, a determination is made as to whether these rolling statistics are significant. If they are, the result is scored in step 416.

The series from step 406 are also used to calculate the t-value from the whole array and the sub-series (step 418). In step 420 this t-value is compared to a threshold. If it is larger, in step 422 the result is scored.

Finally, in step 426 the localized zero-crossings are computed and in step 428 the result is scored.

The four parallel branches of the flow chart of FIG. 9 correspond to the four statistical tests described above.

In step 430 a predetermined formula is used to combine the scored results from the four tests. For example, the tests can be weighted, and in step 430 a weighted average is calculated. Alternatively, a set of fuzzy logic rules can be used to combine the four scores.

In step 432 the result of the determination in step 430 is used to determine the presence or absence of TWA. In addition, in step 434 the results of the tests are used to compute the characteristics of the TWA.

Getting back to FIG. 7, the decision I and II correspond to the decisions in step 328 and 432 respectively. Decision I is the decision based on the output of periodic transform values and the decision II is the decision based on the statistical tests 1–4. In step 214 a combined final decision is made as to the presence of TWA. All or some of the statistical tests may be included for making a final decision. A logical combination using AND/OR statements can also be used to arrive at the final decision.

Several variations can be used to implement the processes shown in FIGS. 7, 8 and 9. The choice of number of beats needed for decision-making and the threshold values of the statistical and periodicity transform parameters are subjected to sample data sets and experimentation. Different decision making strategies can be used for different scenarios. In all the cases, a positive decision indicates the presence of alternans and a negative decision indicates the absence of alternans.

Case 1: Increasing Weights for Tests—Different Weights

In this approach, test for difference in means is given the lowest weight (test1) and is followed by Test for sum of adjacent weights (test 2) and so on. For example, let the weights for test1, test2, test3, test4 and test 5 be respectively 0.1,0.2,0.25,0.15 and 0.30, and the tests indicate POSITIVE, NEGATIVE, POSITIVE, POSITIVE and POSITIVE, for the presence of alternans, the final score becomes weight1+weight3+weight4+weight5=0.8 and is above a preset threshold of 0.5 and hence the conclusion is POSITIVE.

Case 2: Equal Weights for All the Tests

In this approach, all the tests, namely test1, test2, . . . , test5, are given equal weights of 0.2. Out of five tests, if three tests or more provide POSITIVE identification for alternans, then the overall result is POSITIVE from the group of tests.

Case 3: Majority of the Tests Showing Positive

This case is equivalent to previous one, case 2. Whenever three, or four or five tests show POSITIVE, the overall conclusion becomes POSITIVE.

Case 4: Equal Weights to All the Statistical Tests and Periodicity Transform

In this approach, the weights for all the statistical tests combined is 0.5 and the weight for the periodicity transform is 0.5. Here, the periodicity transform, being more sensitive, is given the maximum weight and the four statistical tests together are given the same weight as a single periodicity transform result. Hence, in this case, POSITIVE identification of alternans by periodicity transform overrides all other test results.

Case 5: Throwing Away the Results of Some of the Tests

In this approach, the results from the tests are monitored and if they are inconsistent, for example from one experiment to another and/or with the results of the other tests, the results from these tests are discarded. based on inconsistent performance or noisy data.

Case 6: Making Use of Only One Test

This approach is an extreme case where only the test with maximum sensitivity and specificity is chosen and all other tests are discarded or ignored. Case 6 is a subset of case 5.

Numerous modifications may be made to the invention without departing from its scope as defined in the appended claims.

We claim:

1. An apparatus for detecting TWA in potential cardiac patients comprising:
   a sensor adapted to sense an ECG from a patient;
   a T wave detector adapted to detect a plurality of T waves in said ECG;
   an analyzer adapted to perform at least one of a statistical test tests and a periodicity transform on characteristics of said T waves to make a decision on whether TWA are present or not; and
   a template generator adapted to generate a template for said T waves based on the characteristics of a plurality of T waves;
   wherein said analyzer is adapted to determine said characteristic for a plurality of consecutive T waves to form a series, said analyzer being adapted to operate on said series; and to perform at least one of the following statistical tests: difference in means, adjacent values, Raleigh and number of zero crossings
   wherein said T wave detector is adapted to detect at least one of the following T wave characteristics: peak value, area under the T wave, curvature, ST segment slope, and area of smaller T wave segments.

2. The apparatus of claim 1 further comprising a comparator adapted to compare a current T wave to said template, and to reject said current T waves from processing if it differs substantially from said template.

3. An apparatus for detecting TWA in potential cardiac patients comprising:
   a sensor adapted to sense an ECG from a patient;
   a T wave detector adapted to detect a plurality of T waves in said ECG;

an analyzer adapted to perform at least one of a statistical test and a periodicity transform on characteristics of said T waves to make a decision on whether TWA are present or not;

wherein said analyzer performs both said statistical test and said periodicity transform, said analyzer including a combining element adapted to combine the results of said tests to generate said decision.

4. An apparatus for detecting TWA in potential cardiac patients comprising:

a sensor adapted to sense an ECG from a patient;

a T wave detector adapted to detect a plurality of T waves in said ECG;

an analyzer adapted to perform at least one of a statistical test and a periodicity transform on characteristics of said T waves to make a decision on whether TWA are present or not; and a template generator adapted to generate a template for said T waves based on the characteristics of a plurality of T waves;

wherein said T wave detector is adapted to detect at least one of the following T wave characteristics: peak value, area under the T wave, curvature, ST segment slope, and area of smaller T wave segments;

wherein said analyzer is adapted to determine said characteristic for a plurality of consecutive T waves to form a series, said analyzer being adapted to operate on said series.

5. The apparatus of claim 4 further comprising a template generator adapted to generate a template for said T waves based on the characteristics of a plurality of T waves.

6. The apparatus of claim 4 further comprising a comparator adapted to compare a current T wave to said template, and to reject said current T waves from processing if it differs substantially from said template.

7. An apparatus for detecting TWA in potential cardiac patients comprising:

a sensor adapted to sense an ECG from a patient;

a T wave detector adapted to detect a plurality of T waves in said ECG;

an analyzer adapted to perform at least one of a statistical test tests and a periodicity transform on characteristics of said T waves to make a decision on whether TWA are present or not; and a template generator adapted to generate a template for said T waves based on the characteristics of a plurality of T waves.

8. The apparatus of claim 7 further comprising a comparator adapted to compare a current T wave to said template, and to reject said current T waves from processing if it differs substantially from said template.

9. An apparatus for detecting TWA in potential cardiac patients comprising:

a sensor adapted to sense an ECG from a patient;

a T wave detector adapted to detect a plurality of T waves in said ECG;

an analyzer adapted to perform at least one of a statistical test and a periodicity transform on characteristics of said T waves to make a decision on whether TWA are present or not; and a template generator adapted to generate a template for said T waves based on the characteristics of a plurality of T waves.

10. The apparatus of claim 9 further comprising a comparator adapted to compare a current T wave to said template, and to reject said current T waves from processing if it differs substantially from said template.

* * * * *